US009067855B2

(12) United States Patent
Grandbois et al.

(10) Patent No.: US 9,067,855 B2
(45) Date of Patent: Jun. 30, 2015

(54) PROCESS FOR THE PRODUCTION OF CHLORINATED ALKANES

(71) Applicants: Matthew L. Grandbois, Midland, MI (US); William J. Kruper, Jr., Sanford, MI (US)

(72) Inventors: Matthew L. Grandbois, Midland, MI (US); William J. Kruper, Jr., Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/358,079

(22) PCT Filed: Nov. 13, 2012

(86) PCT No.: PCT/US2012/064792
§ 371 (c)(1),
(2) Date: May 14, 2014

(87) PCT Pub. No.: WO2013/078035
PCT Pub. Date: May 30, 2013

(65) Prior Publication Data
US 2015/0045592 A1    Feb. 12, 2015

Related U.S. Application Data

(60) Provisional application No. 61/562,025, filed on Nov. 21, 2011.

(51) Int. Cl.
*C07C 17/013* (2006.01)
*C07C 17/10* (2006.01)

(52) U.S. Cl.
CPC ............... *C07C 17/013* (2013.01); *C07C 17/10* (2013.01)

(58) Field of Classification Search
CPC .............................. C07C 17/013; C07C 17/10
USPC .......................................................... 570/261
See application file for complete search history.

(56) References Cited

U.S. PATENT DOCUMENTS

| | | | |
|---|---|---|---|
| 2,119,484 A | 5/1938 | Levine |
| 2,179,378 A | 11/1939 | Metzger |
| 2,207,193 A | 7/1940 | Groll |
| 2,299,441 A | 10/1942 | Vaughan |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl Hans et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,926,758 A | 12/1975 | Smith |
| 3,948,858 A | 4/1976 | Weirsum |
| 3,954,410 A | 5/1976 | Pohl |
| 4,038,372 A | 7/1977 | Colli |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |

(Continued)

FOREIGN PATENT DOCUMENTS

| | | |
|---|---|---|
| CH | 609022 | 6/1974 |
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |

(Continued)

OTHER PUBLICATIONS

Bai et al, "Isomerization of Tetrachloropropene to Promote Utilization Ratio of Triallate Raw Materials", Petrochemical Technology & Application, 2007, 25(1).

(Continued)

*Primary Examiner* — Shailendra Kumar
(74) *Attorney, Agent, or Firm* — Susan M. Zerull; KSJLAW, LLC

(57) ABSTRACT

Processes for the production of chlorinated alkanes are provided. The present processes comprise reacting one or more mono- and/or dichloroalkanes to form tri-, tetra- and/or pentachloroalkanes, with high regioselectivity. In those embodiments wherein a dichloroalkane is desirably utilized, it may advantageously be a vicinal dichloroalkane. Further, only one catalyst is utilized. The present processes make use of sulfuryl chloride as a chlorinating agent, rather than a gaseous chlorinating agent such as chlorine gas. Finally, the process uses lower intensity process conditions than at least some conventional processes, and thus, operating costs are saved.

14 Claims, No Drawings

(56) References Cited

U.S. PATENT DOCUMENTS

| | | |
|---|---|---|
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel |
| 8,058,490 B2 | 11/2011 | Strebelle |
| 8,071,825 B2 | 12/2011 | Johnson |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Kruper |
| 8,258,355 B2 | 9/2012 | Merkel |
| 8,357,828 B2 | 1/2013 | Okamoto |
| 8,367,867 B2 | 2/2013 | Zardi |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,581,011 B2 | 11/2013 | Tirtowidjojo |
| 8,581,012 B2 | 11/2013 | Tirtowidjojo |
| 8,614,361 B2 | 12/2013 | Suzuki |
| 8,614,363 B2 | 12/2013 | Wilson |
| 2001/0018962 A1 | 9/2001 | Joshi |
| 2002/0110711 A1 | 8/2002 | Boneberg |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0172472 A1 | 7/2011 | Sakyu |
| 2011/0218369 A1 | 9/2011 | Elsheikh |
| 2011/0251425 A1 | 10/2011 | Penzel |
| 2012/0065434 A1 | 3/2012 | Nose |
| 2014/0081055 A1 | 3/2014 | Tirtowidjojo |

FOREIGN PATENT DOCUMENTS

| | | |
|---|---|---|
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 A2 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |

(56) References Cited

FOREIGN PATENT DOCUMENTS

| WO | 2011065574 | 6/2011 |
|---|---|---|
| WO | 2012011844 | 1/2012 |
| WO | 2012081482 | 6/2012 |
| WO | 2012166393 | 12/2012 |

OTHER PUBLICATIONS

Boualy et al, "Kharasch Addition of Tetrachloromethane to Alkenes Catalyzed by Metal Acetylacetonates", Catalysis Communications, 2011, pp. 1295-1297, vol. 12.

Chai et al., "Study of Preparation of 1,1,1,3-tetrachloropropane", Zhejiang Chemical Industry, 2010, pp. 1-3, 41(5).

Cristiano et al., "Tetraalkylphosphonium Trihalides. Room Temperature Ionic Liquids as Halogenation Reagents", J. Org. Chem., 2009, pp. 9027-9033, vol. 74.

Evstigneev et al., "Initiated Chlorination of Tetrachloropropane", Khim. Prom., 1984, pp. 393-394, 16(7).

Galitzenstein et al., "The Dehydrochlorination of Propylene Dichloride", Journal of the Society of Chemical Industry, 1950, pp. 298-304, vol. 69.

Gault et al., "Chlorination of Chloroform", Comptes Rendus Des Seances De L'Academie des Sciences, 1924, pp. 467-469, vol. 179.

Gerding et al., "Raman Spectra of aliphatic chlorine compounds II. Chloroethenes and Chloropropenes", Recueil, Jan. 1, 1955, pp. 957-975, vol. 74.

Hatch et al., "Allylic Chlorides. XV. Preparation and Properties of the 1,2,3-Trichloropropenes", JACS, Jan. 5, 1952, pp. 123-126, 74(1).

Hatch et al., "Allylic Chlorides. XVIII. Preparation and Properties of 1,1,3-tricholoro-2-fluoro-1-propene and 1,1,2,3- tetrachloro-1-propene", JACS, Jul. 5, 1952, pp. 3328-3330, 74(13).

Herzfelder, "Substitution in the Aliphatic Series", Berichte der Deutschen Chemischen Gesellschaft, May-Aug. 1893, pp. 1257-1261, 26(2).

Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).

Kang et al., "Kinetics of Synthesis of 1,1,1,3,3-pentachlorobutane Catalyzed by Fe-FeCl3", Chemical Research and Application, Jun. 2011, pp. 657-660, 23(6).

Kharasch et al., "Chlorinations with Sulfuryl Chloride. I. The Peroxide-Catalyzed Chlorination of Hydrocarbons", JACS, 1939, pp. 2142-2150, vol. 61.

Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper et al., "Synthesis of alpha-Halocinnamate Esters via Solvolytic Rearrangement of Trichloroallyl Alcohols", J. Org. Chem., 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al., "Thermocatalytic Reactions of Bromochloropropanes", Russian Journal of Physical Chemistry, Jan. 1, 1983, pp. 1142-1146, vol. 57.

Liu et al., "Progress in the Synthesis of 1,1,1,3-tetrachloropropane", Guangzhou Chemicals, 2011, pp. 41-42, 39(5).

McBee et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.

Nikishin et al., "Reactions of Methanol and Ethanol", Seriya Khimicheskaya, Dec. 1966, pp. 2188-2192, vol. 12.

Pozdnev et al., "Chlorination of Chloroform and the Conversion of Methylene Chloride Manufacture Still Residues", Khim., Khim. Tekhnol., 1970, 70(4).

Rotshtein et al., "Isomer Distribution on Chlorination of Chloropropanes", Zhurnal Organicheskoi Khimii, Sep. 1966, pp. 1539-1542, 2(9).

Semenov et al., "Selectivity of Photochemical Chlorination of Chloromethane in the Liquid Phase", Zhurnal Prikladnoi Khimii, Apr. 1985, pp. 840-845, 58(4).

Shelton et al., "Addition of Halogens and Halogen Compounds to Allylic Chlorides. I. Addition of Hydrogen Halides", Journal of Organic Chemistry, Sep. 1958, pp. 1876-1880, vol. 23.

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al., "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

Stevens, "Some New Cyclopropanes with a Note on the Exterior Valence Angles of Cyclopropane", JACS, Vo. 68, No. 4, 1945, 620-622.

Fields et al., "Thermal Isomerization of 1,1-dichlorocyclopropanes", Chemical Communications (London) No. 21, Jan. 1, 1967, p. 1081.

Nguyen et al., "Condensation de chloroforme avec des olefins fluourees en milieu basique", Journal of Flourine Chemistry, vol. 55, No. 3, Dec. 1, 1991, pp. 241-248.

Tobey et al., Pentachlorocyclopropane 1, Journal of the American Chemical Society, vol. 88, No. 11, Jun. 1, 1996, pp. 2478-2481.

Ochi, et al., "Preparation of Chloropropenes by Photochemical Dehydrochlorination of 1,2-Dichloropropane", Chemical Abstracts, Jul. 17, 1989, p. 574, 111(3).

PROCESS FOR THE PRODUCTION OF CHLORINATED ALKANES

This application is a 371 of PCT/US2012/064792, filed Nov. 13, 2012, which claims benefit of 61/562,025, filed Nov. 21, 2011.

FIELD

The present invention relates to processes for the production of chlorinated alkanes, and in particular, to processes for the production of tri-, tetra- and pentachlorinated alkanes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, highly chlorinated alkanes, e.g., tri-, tetra- and pentachloroalkanes.

Unfortunately, these higher chlorides have proven difficult to manufacture using acceptable process conditions and in commercially acceptable regioselectivities and yields. For example, conventional processes for the production of trichloropropane (such as those disclosed in U.S. Pat. No. 2,119,484 and U.S. Pat. No. 4,051,182) provide unacceptable selectivity to the desired trichloropropane isomer, make use of suboptimal chlorinating agents, and/or require the use of expensive catalyst systems and/or initiators.

It would thus be desirable to provide improved processes for the production of chlorocarbon precursors useful as feedstocks in the synthesis of refrigerants and other commercial products. More particularly, such processes would provide an improvement over the current state of the art if they provided a higher regioselectivity relative to conventional methods, made use of optimal chlorinating agents and/or made use of less expensive catalyst systems and/or initiators.

BRIEF DESCRIPTION

The present invention provides efficient processes for the production of chlorinated alkanes. More particularly, the processes make use of one or more mono- and/or dichloroalkanes to produce tri-, tetra-, and pentachloroalkanes with high selectivity. In some embodiments, the processes advantageously make use of 1,2-dichloropropane, a by-product in the production of chlorohydrin, as a low cost starting material. Selectivity of the process is enhanced over conventional chlorination processes by employing a Lewis acid as an ionic chlorination catalyst, instead of the catalyst systems comprising multiple catalysts required by the conventional processes. Further cost savings are provided in that low intensity process conditions, e.g., low temperatures, ambient pressure and minimal reactor residence time, are utilized.

In one aspect, the present invention provides a process for the production of tri-, tetra, and/or pentachlorinated alkanes from one or more mono and/or dichlorinated alkanes. The process comprises chlorinating the one or more mono and/or dichlorinated alkane in the presence of one ionic chlorination catalyst. In some embodiments, the mono and/or dichlorinated alkane is a vicinal dichlorinated alkane, e.g., a 1,2-dichloroalkane, and in such embodiments, the corresponding trichlorinated alkane, e.g., a 1,1,2-trichloroalkane, may be produced with a regioselectivity of at least 20:1, or at least 30:1, or at least 40:1, or even at least 50:1. In some embodiments, the dichlorinated alkane may be 1,2-dichloropropane and the trichlorinated alkane may be 1,1,2-trichloropropane. The chlorinating agent is desirably a liquid, and in some embodiments, may desirably be sulfuryl chloride. The ionic chlorination catalyst is desirably a Lewis acid catalyst, such as aluminum chloride, and advantageously, the process requires only the use of one such catalyst. The process is desirably conducted at low intensity conditions, e.g., a reaction temperature of from 55° C. to 65° C., ambient pressure, and with a reactor residence time of 1 hour or less.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Throughout the specification, "PDC" may be used herein as an abbreviation for 1,2-dichloropropane and "TCP" may be used as an abbreviation for 1,2,3-trichloropropane.

The present invention provides efficient processes for the production of chlorinated alkanes. The present processes comprise reacting one or more mono- and/or dichloroalkanes to tri-, tetra- and/or pentachloroalkanes, with high regioselectivity, e.g., to 1,1,2-trichloroalkanes, 1,2,2,3-tetrachloropropane and/or 1,1,2,2,3-pentachloropropane. Advantageously, only one catalyst is required, and desirably comprises a Lewis acid catalyst. Furthermore, the present processes make use of sulfuryl chloride as a chlorinating agent, rather than a gaseous chlorinating agent such as chlorine gas. The use of sulfuryl chloride is not only advantageous in that it is easier to transport and utilize than gaseous chlorinating agents, but also because, since it is a liquid, it can also serve as a solvent for the reaction and desired catalyst. Finally, the process uses lower intensity process conditions than at least some conventional processes, and thus, operating costs are saved.

The present process can make use of one or more mono- and/or dichlorinated alkanes to produce the desired tri-, tetra- and or pentachlorinated alkanes. Desirably, at least one of the chlorinated alkanes is a vicinal dichlorinated alkane, i.e., the chlorine atoms are present on adjacent carbon atoms. The use of vicinal dichlorinated alkanes is advantageous in that it contributes to the regioselectivity provided by the process.

Any alkane can be utilized in the process, although alkanes comprising from 2-10 carbon atoms, or from 2-8 carbon atoms, or from 2-6 carbon atoms, or from 2-5 carbon atoms, or from 2-4 carbon atoms, or from 2-3 carbon atoms, are particularly suitable. In some embodiments, one of the mono- and/or dichlorinated alkanes comprises mono- or dichlorinated propane, and in those embodiments wherein the dichlorinated alkane is desirably vicinal, comprises 1,2-dichloropropane. The use of 1,2-dichloropropane as a feedstock for the process is advantageous, since it may be available at low cost due to its production as a by-product in many chlorohydrin processes. The one or more mono- and/or dichlorinated alkanes may be generated within the process, if desired, by any methods known to those of ordinary skill in the art.

The tri-, tetra-, and/or pentachlorinated alkane produced by the process will depend upon the mono- and/or dichlorinated alkane used as a starting material, and so, in some embodiments, and due to the commercial significance of trichlorinated ethanes, propanes and butanes, the use of one or more mono and/or dichlorinated ethanes, propanes and butanes as starting materials may be preferred. In some embodiments, 1,2-dichloropropane is utilized as a starting material to produce 1,1,2-trichloropropane at high selectivity, while in others a combination of monochloropropane and 1,2-dichloropropane is utilized as a starting material to produce 1,2,2,3-tetrachloropropane and/or 1,1,1,2,3-pentachloropropane and 1,1,2,2,3-pentachloropropane.

The one or more chlorinated alkane is advantageously chlorinated using a liquid chlorinating agent, such as sulfuryl chloride. The use of a liquid chlorinating agent is advantageous compared to the use of a gaseous chlorinating agent, such as chlorine gas, since a liquid is easier to transport and/or handle than a gaseous chlorinating agent. Chlorine gas in particular, can present a safety hazard. Liquid chlorinating agents, and in particular, sulfuryl chloride ($SO_2Cl_2$), can also act as a solvent for certain catalyst systems and/or reactions, thereby assisting in the provision of an acceptable reaction rate and/or yield. And so, in some embodiments, sulfuryl chloride may desirably be used as the chlorinating agent.

The specificity of the process is further enhanced by the use of a Lewis acid as an ionic chlorination catalyst. It has now been surprisingly discovered that, e.g., anhydrous aluminum chloride, although known as a component of a multicatalyst system for the chlorination of alkanes, when used alone, assists in providing a high degree of specificity to the desired tri-, tetra- and/or pentachloroalkane, e.g., a 1,1,2-trichloroalkane, 1,2,2,3-tetrachloropropane and/or 1,1,2,2,3-pentachloropropane. More particularly, aluminum chloride has conventionally been utilized with at least one other catalyst, oftentimes iodine and/or ferric chloride, as a component of a free radical initiator system that often requires the additional use of an initiator, such as ultraviolet light. In contrast, the present inventors have now discovered that aluminum chloride may be used as an ionic chlorination catalyst, and in combination with sulfuryl chloride as a chlorinated agent, acts to transform one or more mono- and/or dichloroalkanes, which in some embodiments may comprise a vicinal dichloroalkane, to the corresponding 1,1,2-trichloroalkane, 1,2,2,3-tetrachloropropane and/or 1,1,2,2,3-pentachloropropane with regioselectivities of greater than 10:1, or greater than 20:1 or greater than 30:1 or even at a 40:1 ratio, or greater, over other tri-, tetra- and pentachloroalkane products.

Generally speaking, enough of the catalyst should be utilized to provide some improvement to reaction process conditions (e.g., a reduction in required temperature) and desirably, reaction selectivity, but yet not be more than will provide any additional benefit, if only for reasons of economic practicality. For purposes of illustration only, then, it is expected that useful concentrations of anhydrous aluminum chloride will range from 0.01% to 20% by weight each with respect to the mono and/or dichlorinated alkane(s), or from 0.1% to 10%, or from 1% to 5 wt. %, inclusive of all subranges there between.

The reaction conditions under which the process is carried out are advantageously low intensity. That is, low temperatures, e.g., of less than 100° C., or less than 90° C., or less than 80° C. or less than 70° C., or less than 60° C., or less than 50° C., or even as low as 40° C. may be utilized and the desired selectivities to the tri-, tetra-, and/or pentachloroalkanes yet be realized. In some embodiments, temperatures of from 40° C. to 70° C., or 55° C. to 65° C. may be utilized. Similarly, ambient pressure is suitable for carrying out the process, or pressures within 250, or 200, or 150, or 100, or 50, or 40, or 30, or 20, or even 10 psi, of ambient are suitable. Reactor occupancy may also be minimized with the desired selectivities yet seen—for example, reactor occupancy times of less than 20 hours, or less than 15 hours, or less than 10 hours, or less than 5 hours, or less than 4, 3, 2, or even 1 hour, are possible. The reactor may be any suitable liquid phase reactor, such as a batch or continuous stirred tank autoclave reactor with an internal cooling coil. A shell and multitube exchanger followed by vapor liquid disengagement tank or vessel can also be used.

In one exemplary process, 1,2-dichloropropane is converted to 1,1,2-trichloropropane at selectivities of, e.g., 40:1 over other trichloroalkane products, by reacting 1,2-dichloropropane with sulfuryl chloride in the present of aluminum chloride at a temperature of from 55° C. to 65° C., ambient pressure and a reactor occupancy of less than one hour.

In another exemplary process, monochloropropane is converted 1,1,2,2,3-pentachloropropane at selectivities of, e.g., 40:1 over other trichloroalkane products, by reacting monochloropropane with sulfuryl chloride in the presence of aluminum chloride at a temperature of from 55° C. to 65° C., ambient pressure, and a reactor occupancy of 24-48 hours.

Some embodiments of the invention will now be described in detail in the following examples.

Example 1

Ionic Chlorination of PDC to TCP Using Aluminum Chloride as Catalyst and Sulfuryl Chloride as Chlorinating Agent Liquid sulfuryl chloride and PDC (1,2-dichloropropane) are mixed in a 100 ml flask heated in a water bath to maintain temperature 55° C.-60° C. in the presence of aluminum chloride ($AlCl_3$) catalyst. A reflux column is placed to return unreacted reactants as well the reaction intermediate 1-chloropropene to the reaction liquid while the HCl and $SO_2$ byproducts are released to a caustic scrubber at the top of the reflux column. Gas chromatography coupled with mass spectroscopy is used to determine the product composition.

After 30 minutes of reaction time in 40 mole % of $AlCl_3$ the product mixture was found to be 1,1,2-trichloropropane and 1,2,3-trichloropropane at molar ratio of 40 to 1.

Example 2-Comparative

Chlorination of PDC to TCP Using Aluminum Chloride as Catalyst and Chlorine Gas as Chlorinating Agent Liquid PDC and an inert solvent, carbon tetrachloride, are mixed in a 100 ml flask heated in a water bath to maintain a temperature of 55° C.-60° C. in the presence of $AlCl_3$ catalyst. A reflux column is placed to return unreacted reactants. Gaseous chlorine is bubbled into the liquid phase. Gas chromatography coupled with mass spectroscopy is used to determine the product composition.

After 60 minutes of reaction time in 10 mole % of $AlCl_3$ the product mixture was found to be 1,1,2-trichloropropane and 1,2,3-trichloropropane at molar ratio of 8 to 1.

Example 3-Comparative

Chlorination of PDC to TCP Using Aluminum Chloride and Iodine as Catalyst and Sulfuryl Chloride as Chlorinating Agent Liquid sulfuryl chloride and PDC are mixed in a 100 ml flask heated in a water bath to maintain a temperature of 55° C.-60° C. in the presence of $AlCl_3$ and $I_2$ catalyst. A reflux column is placed to return unreacted reactants. Gaseous chlorine is bubbled into the liquid phase. Gas chromatography coupled with mass spectroscopy is used to determine the product composition.

After 180 minutes of reaction time in 1.2 mole % of $AlCl_3$ and 0.3 mole % of $I_2$ the product mixture was found to be 1,1,2-trichloropropane and 1,2,3-trichloropropane at molar ratio of 4 to 1.

Example 4

Ionic Chlorination of Monochloropropane to TPC Using Aluminum Chloride as Catalyst and Sulfuryl Chloride as Chlorinating Agent Liquid sulfuryl chloride and 2-chloropropane are mixed in a 100 ml flask heated in a water bath to maintain temperature 55° C.-60° C. in the presence of $AlCl_3$ catalyst. A reflux column is placed to return unreacted reactants as well the reaction intermediates to the reaction liquid while the HCl and $SO_2$ byproducts are released to a caustic scrubber at the top of the reflux column. Gas chromatography coupled with mass spectroscopy is used to determine the product composition.

After 120 minutes of reaction time in 40 mole % of $AlCl_3$ the product mixture was found to be 1,1,2-trichloropropane and 1,2,3-trichloropropane at molar ratio of 40 to 1.

Example 5

Ionic Chlorination of PDC to 1,1,2,2,3-Pentachloropropane Using Aluminum Chloride as Catalyst and Sulfuryl Chloride as Chlorinating Agent Liquid sulfuryl chloride and PDC are mixed in a 100 ml flask heated in a water bath to maintain temperature 55° C.-60° C. in the presence of $AlCl_3$ catalyst. A reflux column is placed to return unreacted reactants as well the reaction intermediates to the reaction liquid while the HCl and $SO_2$ byproducts are released to a caustic scrubber at the top of the reflux column. Gas chromatography coupled with mass spectroscopy is used to determine the product composition.

After 17 hours of reaction time in 40 mole % of $AlCl_3$ the product mixture was found to be 1,1,2,2,3-pentachloropropane as the only pentachloropropane.

The invention claimed is:

1. A process for the production of tri-, tetra- and/or pentachlorinated alkanes from one or more mono and/or dichlorinated alkanes comprising chlorinating the mono and/or dichlorinated alkane in the presence of aluminum chloride, wherein the chlorinating agent comprises sulfuryl chloride.

2. The process of claim 1, wherein at least one of the one or more mono- and/or dichlorinated alkanes comprises a vicinal dichloroalkane.

3. The process of claim 1, wherein the dichloroalkane comprises 1,2-dichloropropane.

4. The process of claim 3, wherein the tri-, tetra- and/or pentachlorinated alkane comprises a 1,1,2-trichloroalkane.

5. The process of claim 4, wherein the tri-, tetra- and/or pentachlorinated alkane comprises 1,1,2-trichloropropane.

6. The process of claim 5, wherein selectivity of the process to 1,1,2-trichloropropane is at least 20:1.

7. The process of claim 6, wherein selectivity of the process to 1,1,2-trichloropropane is at least 40:1.

8. The process of claim 3, wherein the tri-, tetra- and/or pentachlorinated alkane comprises a 1,2,2,3-tetrachloroalkane.

9. The process of claim 8, wherein the tri-, tetra- and/or pentachlorinated alkane comprises 1,2,2,3-tetrachloropropane.

10. The process of claim 3, wherein the tri-, tetra- and/or pentachlorinated alkane comprises a 1,1,2,2,3-pentachloroalkane.

11. The process of claim 10, wherein the tri-, tetra- and/or pentachlorinated alkane comprises 1,1,2,2,3-pentachloropropane.

12. The process of claim 1, wherein the process is conducted at a temperature of from 40° C. to 70° C.

13. The process of claim 1, wherein the process is conducted at ambient pressure.

14. The process of claim 1, wherein the process is carried out in a liquid phase reactor, and the reactor residence time is less than 1 hour.

* * * * *